(12) United States Patent
Ghelli et al.

(10) Patent No.: US 8,052,632 B2
(45) Date of Patent: Nov. 8, 2011

(54) CARDIOTOMY RESERVOIR WITH BLOOD INFLOW AND OUTFLOW CONNECTORS LOCATED FOR OPTIMIZING OPERATION

(75) Inventors: Nicola Ghelli, Pietro in Casale (IT); Edgardo Costa Maianti, Mirandola (IT); Roberto Balanzoni, San Giovanni Del Dosso (IT); Antonio Petralia, Lugo (IT)

(73) Assignee: Eurosets S.r.l., Medolla (IT)

( * ) Notice: Subject to any disclaimer, the term of this patent is extended or adjusted under 35 U.S.C. 154(b) by 354 days.

(21) Appl. No.: 12/382,947

(22) Filed: Mar. 27, 2009

(65) Prior Publication Data
US 2009/0259161 A1   Oct. 15, 2009

(30) Foreign Application Priority Data

Apr. 9, 2008 (IT) .............................. MI2008A0622

(51) Int. Cl.
*A61M 37/00* (2006.01)

(52) U.S. Cl. ..................... 604/6.15; 604/4.01; 604/5.01; 604/5.03; 604/6.09

(58) Field of Classification Search ................ 604/4.01, 604/5.01, 5.03, 6.09, 6.15, 7
See application file for complete search history.

(56) References Cited

U.S. PATENT DOCUMENTS 4,157,965 A * 6/1979 Raible .......................... 210/305
5,540,841 A * 7/1996 Gsell et al. .................... 210/645
2005/0131333 A1 * 6/2005 Engstrom .................... 604/5.03

FOREIGN PATENT DOCUMENTS

| EP | 1 040 858 A | 10/2000 |
|---|---|---|
| EP | 1 210 956 A | 6/2002 |
| GB | 2 246 713 A | 2/1992 |

* cited by examiner

*Primary Examiner* — Leslie Deak
(74) *Attorney, Agent, or Firm* — Young & Thompson

(57) ABSTRACT

A cardiotomy reservoir, comprising an outer wall provided, at the lid, with connectors for the inflow of blood to be filtered and, at the bottom, with a connector for the outflow of the filtered blood, a filtering mass being provided which divides the space delimited by the outer wall into a portion that is connected to the inflow connectors and a portion that is connected to the outflow connector; the cardiotomy reservoir comprises a layer of material adapted to retain fats present in blood, and further comprises a first partition and a second partition, which are adapted to delimit at different distances the region that comprises the blood outflow connector and are provided with ports for the passage of the blood in its path for accessing the connector which are arranged at differentiated levels with respect to the bottom, the ports that are provided in the first partition that lies closest to the outflow connector being located at a height, from the bottom, that is greater than the height of the ports provided in the second partition, detachable elements for blocking the blood outflow connector being further provided.

7 Claims, 3 Drawing Sheets

CARDIOTOMY RESERVOIR WITH BLOOD INFLOW AND OUTFLOW CONNECTORS LOCATED FOR OPTIMIZING OPERATION

BACKGROUND OF THE INVENTION

Devices are known as cardiotomy reservoirs that are designed to receive blood collected in the operating field during surgery in order to filter it and return it to the patient after appropriate treatments.

The blood that reaches the cardiotomy reservoir from the operating field may contain fats particularly derived from cuts at the sternum and at the mammary region, which can cause microemboli, with dangerous consequences, such as for example occlusion of brain arteries.

Therefore, these fats must be eliminated from the blood before reinfusion to the patient, and in the background art this is done by means of a layer of non-woven fabric inserted within the filtering mass, which however operates with rather limited effectiveness.

Besides to what is described above, it should be noted that there is the need to control the quantity of leukocytes in the blood, and for this purpose the background art uses a particular filtering material, known as leukocyte filter, which is inserted in a specifically dedicated apparatus that is inserted in the line along which the blood flows.

SUMMARY OF THE INVENTION

The aim of the present invention is therefore to provide a cardiotomy reservoir that has a high efficiency in eliminating the fats that are present in blood.

Within this aim, an object of the invention is to devise a cardiotomy reservoir that is capable of keeping under control the quantity of leukocytes present in blood.

This aim and this object are achieved by a cardiotomy reservoir according to the invention, comprising an outer wall provided, at the lid, with connectors for the inflow of blood to be filtered and, at the bottom, with a connector for the outflow of the filtered blood, a filtering mass being provided which divides the space delimited by said outer wall into a portion that is connected to said inflow connectors and a portion that is connected to said outflow connector, and comprises a layer of material adapted to retain fats present in blood, characterized in that a first partition and a second partition are provided, which are adapted to delimit at different distances the region that comprises the blood outflow connector and are provided with ports for the passage of the blood in its path for accessing said connector which are arranged at differentiated levels with respect to the bottom, the ports provided in the first partition that lies closest to the outflow connector being located at a height, from the bottom, that is greater than the height of the ports provided in the second partition, detachable means for blocking said blood outflow connector being further provided.

BRIEF DESCRIPTION OF THE DRAWINGS

Further characteristics and advantages will become better apparent from the description of a preferred but not exclusive embodiment of the cardiotomy reservoir according to the invention, illustrated by way of non-limiting example in the accompanying drawings, wherein.

DESCRIPTION OF THE PREFERRED EMBODIMENTS

Figure 1:
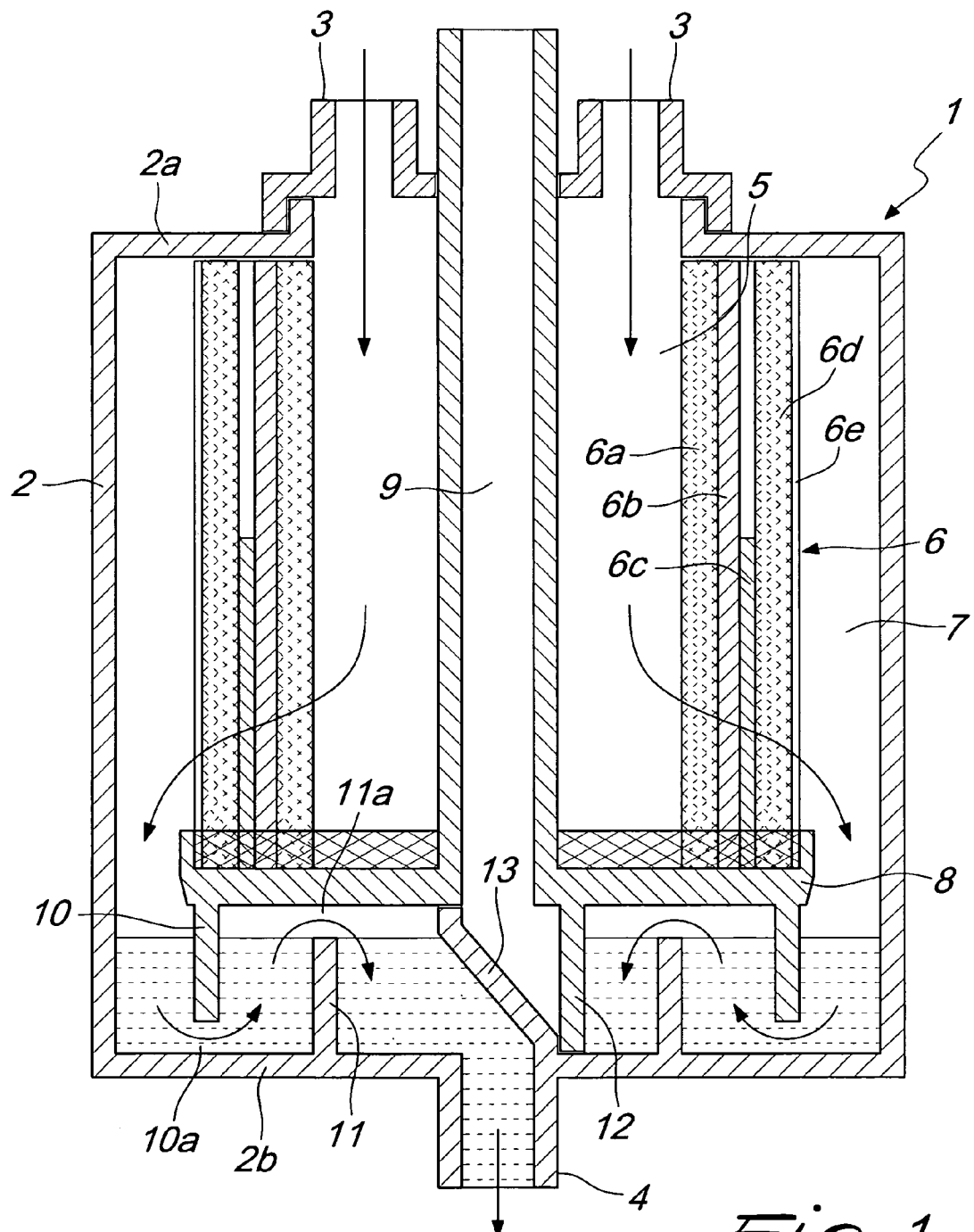
FIG. 1 is a schematic longitudinal sectional view of the cardiotomy reservoir according to the invention.

With reference to the figures, reference numeral 1 generally designates the cardiotomy reservoir, which comprises an outer wall 2 provided, at the lid 2a, with connectors 3 for the inflow of the blood to be filtered that arrives from the operating field and, at a bottom 2b, with a connector 4 for the outflow of the filtered blood.

The blood that enters the cardiotomy reservoir through the connectors 3 enters a portion of space 5, passes through a filtering mass 6 in the form of a cylinder with multiple layers, and reaches a portion of space 7 to reach, in manners specified hereinafter, the outflow connector 4, all according to the arrows shown in the figures.

More precisely, the filtering mass 6 comprises a first defoaming sponge layer 6a, a layer of non-woven fabric 6b adapted to retain fats, a layer of leukocyte filter 6c, a second layer of defoaming sponge 6d, and a containment net 6e.

Figure 4:
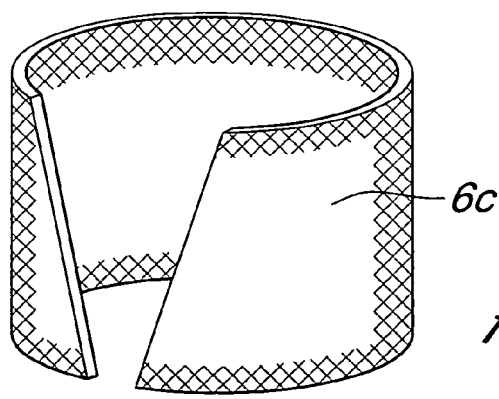
FIG. 4 is a perspective view of a detail of the preceding figures.

The layer 6c of leukocyte filter has a rather high density and is sized with a reduced height with respect to the height of the filtering mass, and with an interruption region, as shown in FIG. 4.

It performs the dual function of controlling the quantity of leukocytes that are present in the blood and also has a synergistic effect with respect to the layer 6b made of non-woven fabric: by way of the slowing undergone by the blood in passing through the layer 6c, the fat retention capacity applied by the layer 6b is in fact enhanced.

The filtering mass 6 is supported by the transverse divider 8 that lies above the bottom 2b, which is monolithically connected to a sleeve 9 that extends along the longitudinal axis of the cardiotomy reservoir, is open at its ends and is capable of rotating about its own axis, obviously entraining with it the transverse divider 8.

An important feature of the cardiotomy reservoir according to the invention consists in the presence of two circumferential partitions 10 and 11, which delimit the region that comprises the blood outflow connector 4.

Figure 3:
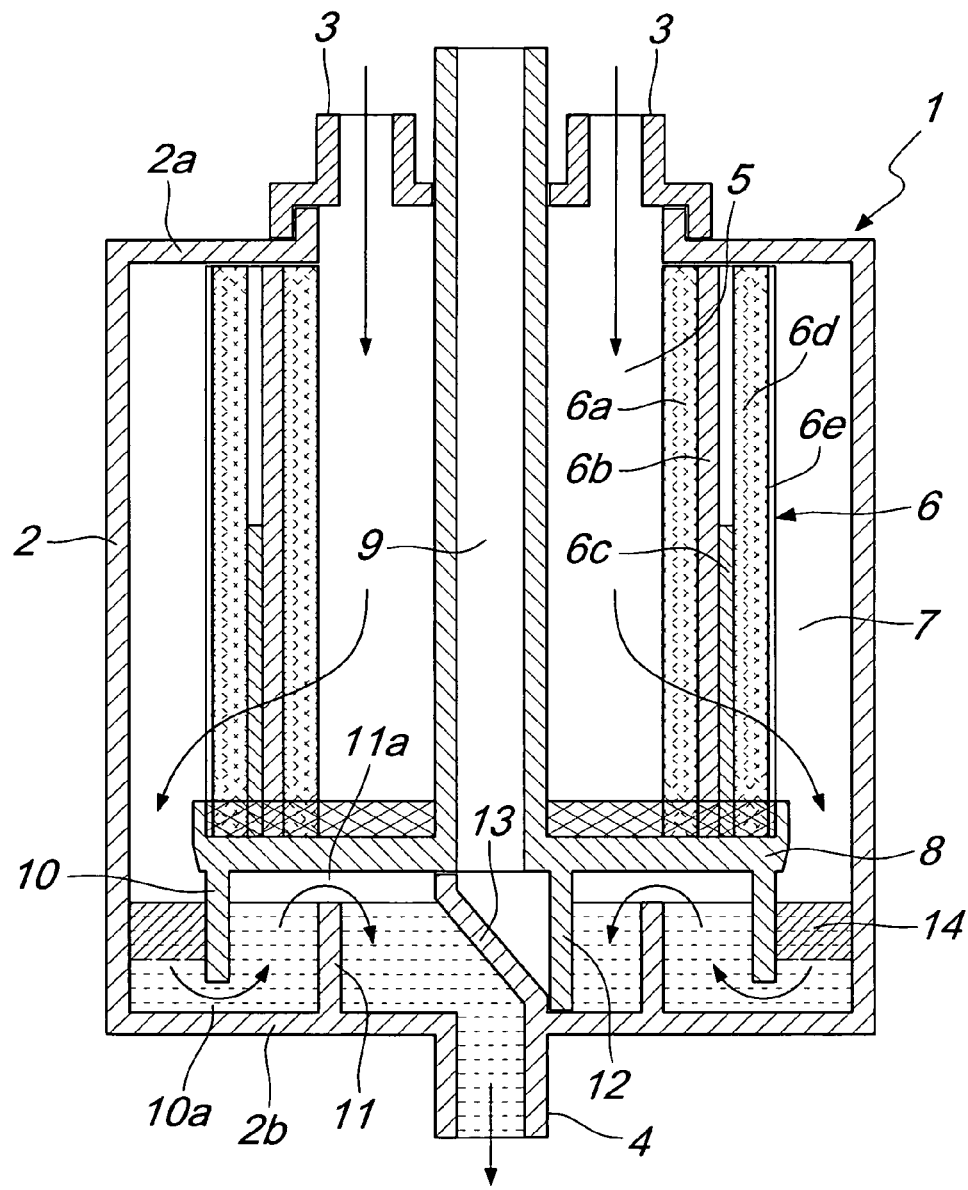

The partition 10 extends monolithically from the transverse divider 8, extending toward the bottom 2b without reaching it, and the partition 11 extends monolithically from the bottom 2b and reaches a certain distance from the transverse divider 8: this leads to the presence of ports 10a, 11a designed to be crossed successively by the blood in its path toward the outflow connector 4, as indicated by the arrows of FIGS. 1 and 3, which are arranged at different heights from the bottom 2b; more precisely, the port 10a provided at the outer partition 10 is at a lower level than the port 11a that is present at the inner partition 11.

Figure 2:
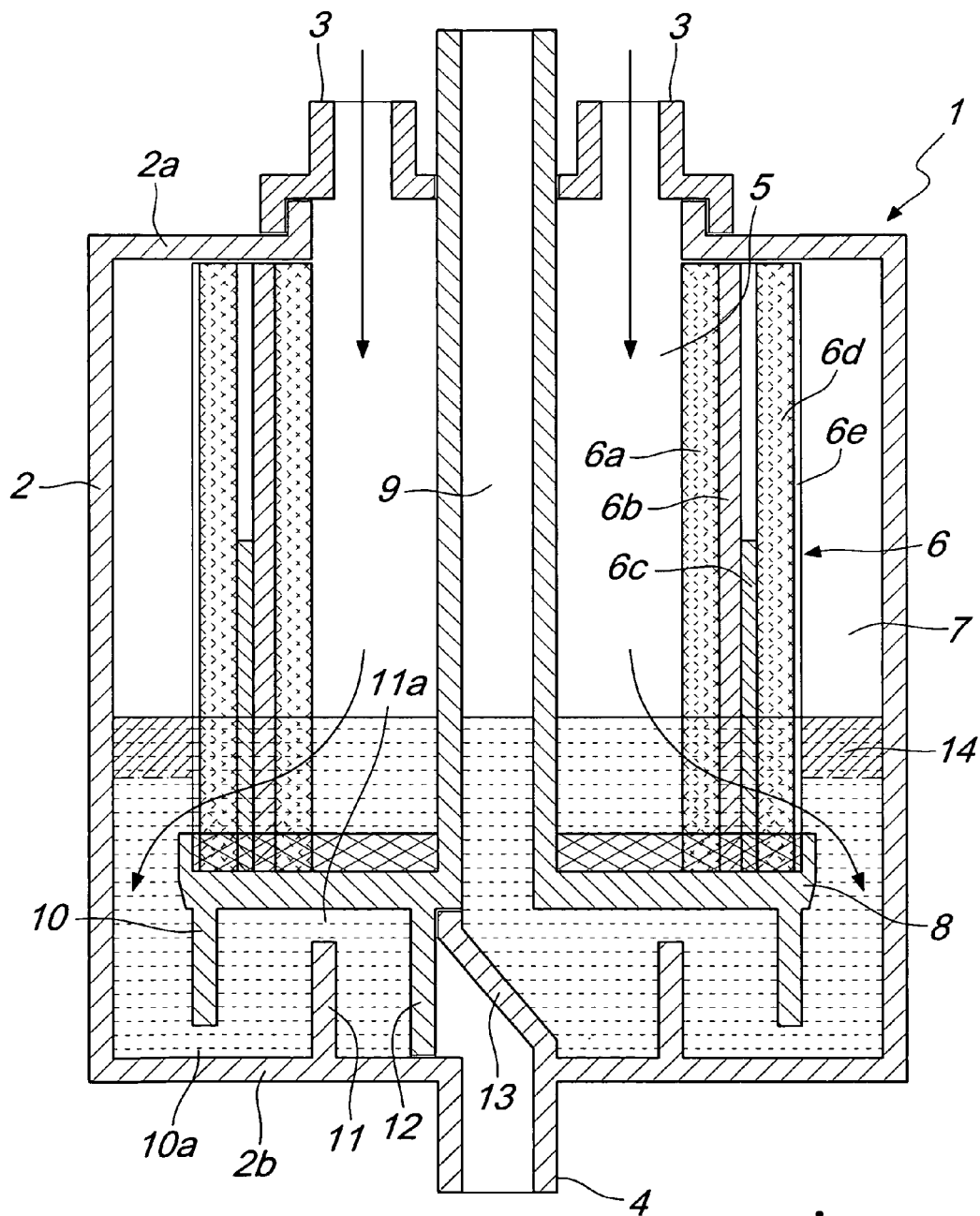
FIGS. 2 and 3 are the same sectional view in different steps of operation.

Finally, the transverse divider 8, is provided with a diaphragm 12, which is adapted to be arranged selectively, following a rotation of the assembly formed by the sleeve 9 and by the divider 8 and by cooperating with a tab 13 that extends from the bottom 2b, in the open position of the connector 4 shown in FIGS. 1 and 3, and in the position for blocking said connector that is shown in FIG. 2, which offers, where desired by operators, the possibility to aspirate blood through the sleeve 9.

Operation of the cardiotomy reservoir according to the invention is evident from the foregoing.

If one does not deem it necessary to utilize the presence of the ports 10a, 11a because the elimination of fats from the blood provided by the layer 6b comprised in the filtering mass 6 is considered sufficient, it is sufficient to keep constantly open, during access to the cardiotomy reservoir of blood through the inflow connectors 3, also the outflow connector 4: the situation shown in FIG. 1 is thus provided, and the presence of the ports 10a, 11a does not affect operation at all.

If instead the outflow connector 4 is closed during access of blood to the cardiotomy reservoir, the situation shown in FIG. 2 occurs: the blood rises in level with respect to the bottom 2b and stratifies, with the lighter fats in the uppermost layer 14.

At a certain point in time, the operator opens the outflow connector 4, providing the situation of FIG. 3: the blood exits from the cardiotomy reservoir, but the layer of fats 14 is retained by the partition 10 according to an interplay of levels regulated by the principle of communicating vessels, so as to be designed to be discarded together with the cardiotomy reservoir at the end of use.

The effect is identical if, at the end of the period of closure of the outflow connector 4, instead of opening said connector, blood is drawn through the sleeve 9, and it is pointed out that the effect of purifying the blood of the fats contained therein provided by the cardiotomy reservoir according to the invention is important.

The described invention is susceptible of numerous modifications and variations, all of which are within the scope of the appended claims: thus, for example, the blood passage ports in the two partitions 10 and 11 may be provided in any manner.

The disclosures in Italian Patent Application No. MI2008A000622 from which this application claims priority are incorporated herein by reference.

What is claimed is:

1. A cardiotomy reservoir, comprising an outer wall, top lid, and bottom, enclosing an interior space;
    wherein the lid comprises connectors for the inflow of blood to be filtered, the bottom comprises a connector for the outflow of filtered blood;
    a filtering mass that divides the interior of the reservoir into a portion connected to the inflow connectors and a portion connected to the outflow connector;
    wherein the filtering mass is configured to retain fats in blood;
    wherein the bottom portion of the reservoir comprises first and second partition members, the location of which form ports, at different heights, that allow flow to the outlet connector;
    wherein the first partition member, which is closest to the outlet connector, defines flow ports located at a height, from the bottom of the reservoir, that is greater than the height of the ports formed by the location of the second partition member; and
    wherein the apparatus further comprises detachable means for blocking said outflow connector.

2. The cardiotomy reservoir according to claim 1, wherein the filtering mass comprises, starting from the portion connected to the inflow connectors, a first layer of defoaming sponge, said layer of material configured to retain fats comprising a nonwoven fabric, a second layer of defoaming sponge, and a containment net.

3. The cardiotomy reservoir according to claim 1, wherein the filtering mass comprises, outside the layer of material adapted to retain fats, a layer of leukocyte filter.

4. The cardiotomy reservoir according to claim 3, wherein the leukocyte filter has a reduced height with respect to the height of the total filtering mass, and comprises a region of interruption formed by a gap in the continuity of the filter layer.

5. The cardiotomy reservoir according to claim 3, wherein the transverse divider is configured to support the filtering mass and is further connected to a sleeve that extends along the longitudinal axis of the reservoir;
    wherein the sleeve comprises an open upper end and a lower end in selective fluid communication with the outlet connector;
    wherein the sleeve comprises a movable diaphragm that is configured, upon rotation of the sleeve, to provide selective fluid communication between the sleeve and the outlet connector, thereby enabling the aspiration of filtered blood from the sleeve.

6. The cardiotomy reservoir according to claim 1, wherein the filtering mass comprises, starting from the portion connected to the inflow connectors, a first layer of defoaming sponge, a layer of non-woven fabric configured to retain fats, a layer of leukocyte filter, a second layer of defoaming sponge, and a containment net.

7. The cardiotomy reservoir according to claim 1, wherein the reservoir comprises a transverse divider spaced from and parallel to the bottom of the reservoir;
    wherein the first partition protrudes from the bottom and reaches toward the transverse divider without reaching the divider, and the second partition extends from the divider without reaching the bottom.

* * * * *